(12) United States Patent
Boulenguez et al.

(10) Patent No.: US 9,814,727 B2
(45) Date of Patent: Nov. 14, 2017

(54) PIPERAZINE PHENOTHIAZINE DERIVATIVES FOR TREATING SPASTICITY

(71) Applicants: UNIVERSITE D'AIX-MARSEILLE, Marseilles (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

(72) Inventors: Pascale Boulenguez, Marseilles (FR); Sylvie Liabeuf, Marseilles (FR); Laëtitia Gourmand, Marseilles (FR); Annelise Viallat-Lieutaud, Marseilles (FR); Laurent Vinay, Marseilles (FR)

(73) Assignees: UNIVERSITE D'AIX-MARSEILLE, Marseilles (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 0 days.

(21) Appl. No.: 15/124,510

(22) PCT Filed: Mar. 10, 2015

(86) PCT No.: PCT/EP2015/054973
§ 371 (c)(1),
(2) Date: Sep. 8, 2016

(87) PCT Pub. No.: WO2015/135947
PCT Pub. Date: Sep. 17, 2015

(65) Prior Publication Data
US 2017/0014421 A1    Jan. 19, 2017

(30) Foreign Application Priority Data
Mar. 10, 2014    (EP) .................................... 14305345

(51) Int. Cl.
*A61K 31/5415*    (2006.01)
*C07D 279/28*    (2006.01)
*C07D 279/18*    (2006.01)

(52) U.S. Cl.
CPC ........ *A61K 31/5415* (2013.01); *C07D 279/18* (2013.01); *C07D 279/28* (2013.01)

(58) Field of Classification Search
CPC . A61K 31/5415; C07D 279/18; C07D 279/28
See application file for complete search history.

(56) References Cited

U.S. PATENT DOCUMENTS

| 2,928,767 A * | 3/1960 | Gulesich .............. A61K 9/0019 514/44 R |
| 3,857,943 A * | 12/1974 | Amin ..................... A61K 31/54 514/226.2 |
| 2006/0276460 A1 | 12/2006 | Callizot et al. |
| 2010/0113563 A1 | 5/2010 | Wang |
| 2011/0052723 A1 | 3/2011 | Baeyens-Cabrera et al. |

FOREIGN PATENT DOCUMENTS

| EP | 1 470 818 | 10/2004 |
| WO | WO 2009/103487 | 8/2009 |

OTHER PUBLICATIONS

International Search Report and Written Opinion of the ISA for PCT/EP2015/054973, mailed Jun. 1, 2015, 14 pages.
Hempel et al., "The phenothiazine-class antipsychotic drugs prochlorperazine and trifluoperazine are potent allosteric modulators of the human P2X7 receptor", Neuropharmacology, vol. 75, Dec. 1, 2013, pp. 365-379.
Chen et al., "Acute Inhibition of Ca2+/Calmodulin-Dependent Protein Kinase II Reverses Experimental Neuropathic Pain in Mice", Journal of Pharmacology and Experimental Therapeutics, vol. 330, No. 2, May 28, 2009, pp. 650-659.
Dong et al., "The antipsychotic drug, fluphenazine, effectively reverses mechanical allodynia in rat models of neuropathic pain", Psychopharmacology, vol. 195, No. 4, Sep. 23, 2007, pp. 559-568.
ACS et al., "Trifluoperazine modulates (3H) Resiniferatoxin Binding by Human and Rat Vanilloid (Capsaicin) Receptors and Affects 45CA Uptake by Adult Rat Dorsal Root Ganglion Neurones", Journal of Pharmacology and Experimental Therapeutics, vol. 274, No. 3, Sep. 1, 1995, pp. 1090-1098.
Bordet et al., "Targeting Neuroprotection as an Alternative Approach to Preventing and Treating Neuropathic Pain", Neurotherapeutics, vol. 6, No. 4, Oct. 1, 2009, pp. 648-662.
Brooks et al., "Arvanil-induced inhibition of spasticity and persistent pain: evidence for therapeutic sites of action different from the vanilloid VR1 receptor and cannabinoid CB1/CB2 receptors", European Journal of Pharmacology, vol. 439, No. 1-3, Mar. 1, 2002, pp. 83-92.
Ashton et al., "Acylthioxanthenes: agents which selectively reduce decerebrate rigidity in the cat", Journal of Medicinal Chemistry, vol. 23, No. 1, Jun. 1, 1980, pp. 653-657.
Kowalski et al., "Flupentixol and trifluperidol reduce secretion of tumor necrosis factor-α and nitric oxide by rat microglial cells", Neurochemistry International, vol. 43, 2003, pp. 173-178.
Leung et al., "TNF-α and neuropathic pain—a review", Journal of Neuroinflammation, vol. 7, No. 27, Apr. 16, 2010, 11 pages.

\* cited by examiner

*Primary Examiner* — Sudhakar Katakam
(74) *Attorney, Agent, or Firm* — Nixon & Vanderhye P.C.

(57) ABSTRACT

The present invention relates to piperazine phenothiazine derivatives useful as therapeutic agents for treating spasticity, particularly following an ischemia or traumatic injury, or compression syndrome. The invention further relates to a pharmaceutical composition comprising a compound of the invention for treating spasticity.

7 Claims, 4 Drawing Sheets

Figure 1D:
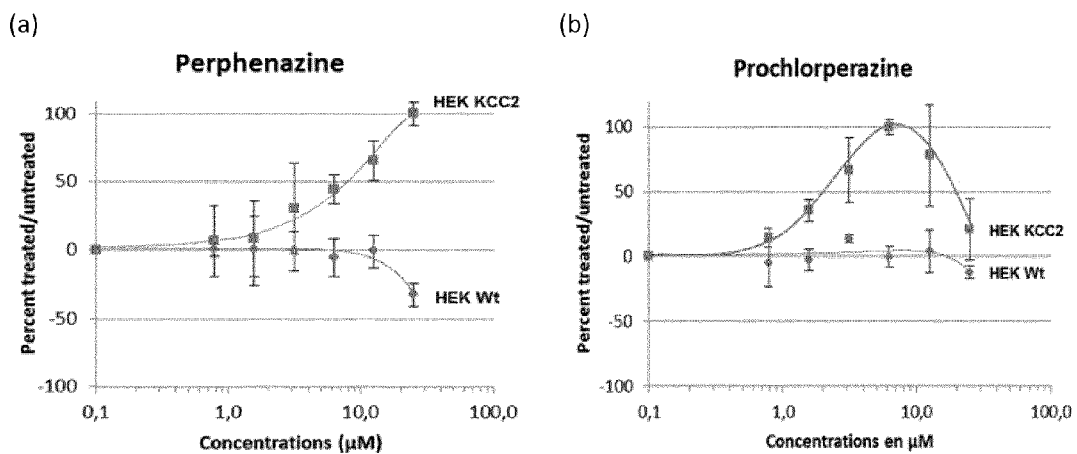

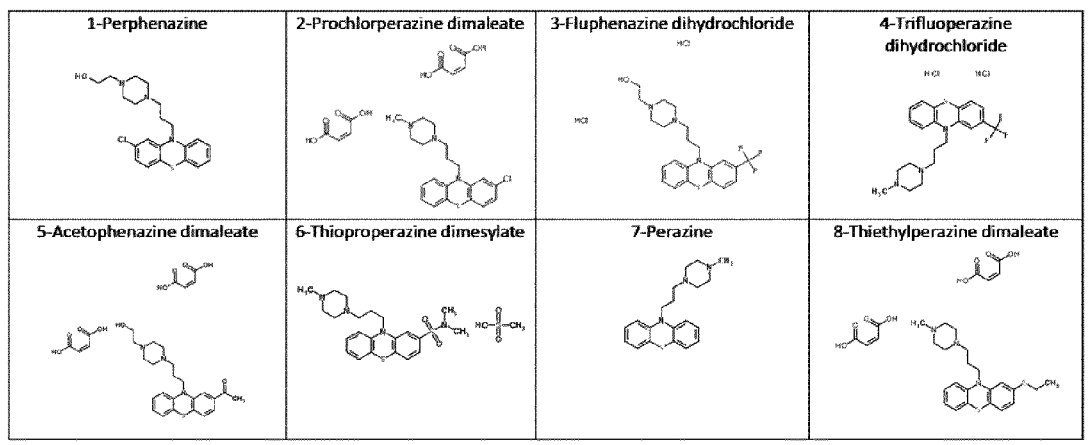
FIGURE 1A
| 1 | TC50 : 50μM | 2 | TC50 > 200μM | 3 | TC50 : 50μM | 4 | TC50 : >200μM |
| 5 | TC50 : 80μM | 6 | TC50 : 80μM | 7 | TC50 : >200μM | 8 | TC50 : 30μM |
FIGURE 1B
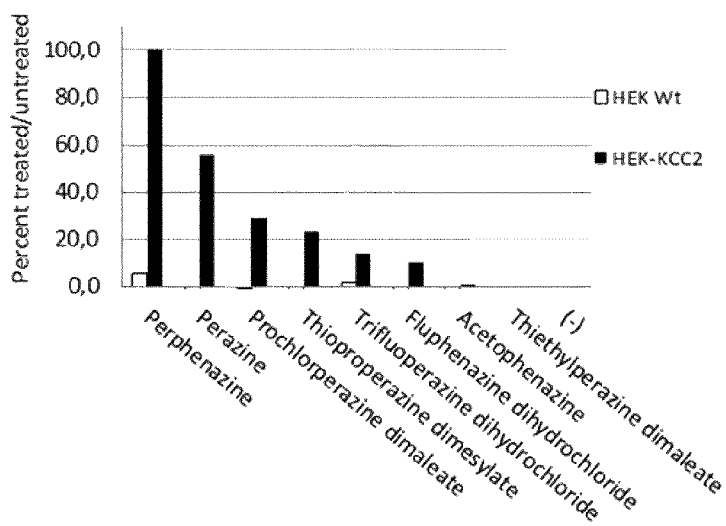
FIGURE 1C

PIPERAZINE PHENOTHIAZINE DERIVATIVES FOR TREATING SPASTICITY

This application is the U.S. national phase of International Application No. PCT/EP2015/054973 filed 10 Mar. 2015, which designated the U.S. and claims priority to EP Patent Application No. 14305345.2 filed 10 Mar. 2014, the entire contents of each of which are hereby incorporated by reference.

FIELD OF THE INVENTION

The present invention relates to the field of medicine, in particular to the use of piperazine phenothiazine derivatives for treating spasticity.

BACKGROUND OF THE INVENTION

Traumatic or ischemic brain, spinal cord and peripheral nervous system injuries involve serious physical (hemiplegia, paraplegia, quadriplegia), sensory (neuropathic pain, numbness, loss of vision) or cognitive (mental changes) consequences for the patient. They are a public health problem as these handicaps generate a loss of autonomy and total dependence requiring heavy medical care throughout life. For example, the economic consequences of a spinal cord injury, including medical and para-medical, home health aides, housing and vehicles changes as well as lost productivity have been estimated to be nearly $10 billion per year in the United States of America (USA). In addition, compression of peripheral nerves by disc herniation causes chronic pain. In the USA, low back pain (also called lumbago) is the fifth most common reason for physician visits. About nine out of ten adults experience back pain at some point in their life, and five out of ten working adults have back pain every year. Low back pain causes 40% of missed days of work in the USA. Also, it is the leading cause of disability worldwide. Herniated disc causing compression of a peripheral nerve is the most common neurologic impairment associated with this condition of low back pain.

Spasticity, characterized by hyperexcitability of the stretch reflex, muscle stiffness, co-contraction of antagonistic muscles and painful spasms, is a common consequence of spinal cord injury (SCI, 75% of patients) or cerebrovascular accident (CVA or stroke). Associated (in the case of SCI) or not (in the case of stroke) with neuropathic pain, it deeply affects the quality of life of patients.

Baclofen is commonly used for treating severe spasticity and can be administered in a patient by means of an implanted pump when the oral administration either becomes inefficient or has too many side effects (such as drowsiness, dizziness . . . ). However, treatments using baclofen are very expensive, even without counting the surgery act for implantation of the pump.

Other drugs such as morphine, gabapentine, pregabaline (Lyrica), clonazepam, diazepam (Valium), and/or ketamin can also be used for treating neuropathic pain and/or spasticity but generally trigger, several side effects as dependency issues. Botulinum toxin (Botox®) intramuscular injection has also showed an effect for treating spasticity in an isolated muscle while provoking weakness of the injected muscle as side effect, which could spread towards neighboring muscles.

As discussed above, no patient's medication is likely to deal effectively and on long-term basis with spasticity while avoiding side effects so that novel therapeutic approaches, drugs, and/or treatments have to be investigated.

Spasticity results from both an increase of excitability of motor neurons and a reduction of the strength of the inhibition in the neural network of the spinal cord. The mechanism responsible for the alteration of neuronal inhibition has recently been identified. The inhibitory action is based on a low chloride ion concentration in target cells (Payne et al., 2003; Vinay, 2008). This low concentration is regulated by proteins specifically expressed in the membrane of neurons, the potassium chloride cotransporter 2 (KCC2), expelling potassium and chloride ions outside cells. The KCC2 expression is greatly decreased after spinal cord injury (Boulenguez et al., 2010). A similar reduction in the amount of KCC2 transporters is also responsible for neuropathic pain after spinal cord injury (Lu et al., 2008; Cramer et al., 2008) or peripheral nerve ligation (Coull et al., 2003; Coull et al., 2005).

Accordingly, KCC2 appears to be an attractive target for treating spasticity or chronic pain but, up to now, no drug or pharmacological tools having a positive activity on KCC2 by increasing expression or functions thereof has been developed yet.

SUMMARY OF THE INVENTION

In this context, the inventors surprisingly identified that compounds of general formula (I), particularly piperazine phenothiazine derivatives activate KCC2 and are useful for treating spasticity or neuropathic pain, particularly following an ischemia or traumatic injury, or a compression syndrome.

The present invention relates to a compound of formula (I):

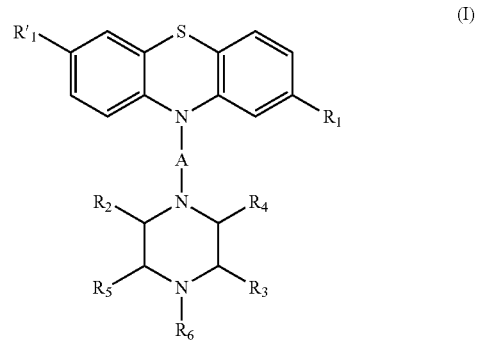

wherein:
A represents a linear or branched ($C_1$-$C_6$) alkyl chain;
$R_1$ represents:
  a hydrogen atom,
  a halogen atom,
  an acyl group CO—$R_7$ or a sulfonyl group $SO_2$—$R_7$, wherein $R_7$ represents a ($C_1$-$C_6$) alkyl group,
  a sulfonamide group $SO_2$—$NR_8R_9$, wherein $R_8$ and $R_9$ independently represent a hydrogen atom or a ($C_1$-$C_6$) alkyl group, or
  a ($C_1$-$C_6$) alkyl, ($C_1$-$C_6$) alkoxy, ($C_1$-$C_6$) alkylmercapto, thio-($C_1$-$C_6$)alkyl or ($C_1$-$C_6$) alkylsulfonyl group, said groups being optionally substituted by at least one halogen atom;
$R_1'$ represents a hydrogen atom or a hydroxyl group, preferably a hydrogen atom;
$R_2$, $R_3$, $R_4$ and $R_5$ are identical or different and each represents a hydrogen atom or a ($C_1$-$C_6$) alkyl group; and $R_6$ represents:
- a hydrogen atom
- a ($C_1$-$C_6$) alkyl group, optionally substituted by at least one hydroxyl group at the end of the alkyl chain,
- a ($C_1$-$C_4$) alkylacyloxy group,
- a ($C_1$-$C_4$) alkyl-$OR_{10}$ group, wherein $R_{10}$ represents:
  - a ($C_1$-$C_4$) alkyl group, optionally substituted by at least one hydroxyl group at the end of the chain, or
  - a $COR_{11}$ group, $R_{11}$ being a ($C_1$-$C_6$) alkyl group optionally substituted by an amino group at the end of the alkyl chain;

or one of its pharmaceutically acceptable salts, for a use for treating spasticity or neuropathic pain, more specifically for a use in the treatment of spasticity.

According to a particular embodiment, the compounds of the invention are of formula (I) where A represents a linear or branched ($C_3$-$C_4$) alkyl chain.

Preferably, $R_1$ represents:
- a hydrogen atom,
- a halogen atom, preferably a chlorine atom,
- an acyl group CO—$R_7$, wherein $R_7$ represents a ($C_1$-$C_6$) alkyl group, preferably a methyl or a n-propyl group,
- a sulfonamide group $SO_2$—$NR_8R_9$ wherein $R_8$ and $R_9$ independently represent a hydrogen atom, or a ($C_1$-$C_6$) alkyl radical, preferably $R_8$ and $R_9$ represent methyl groups,
- a ($C_1$-$C_6$) alkyl group optionally substituted by at least one fluorine atom, preferably a trifluoromethyl group, or
- a thio-($C_1$-$C_6$)alkyl group, preferably a thio-ethyl (—$SCH_2CH_3$) group.

Preferably, $R_1'$, $R_2$, $R_3$, $R_4$ and $R_5$ represent hydrogen atoms.

Preferably, $R_6$ represents:
- a ($C_1$-$C_6$) alkyl group, preferably a methyl or an ethyl group, optionally substituted by at least one hydroxyl group at the end of the alkyl chain,
- an ethyl group substituted by an —$OR_{10}$ group, wherein $R_{10}$ represents:
  - an ethyl group optionally substituted by at least one hydroxyl group at the end of the chain, or
  - a $COR_{11}$ group, $R_{11}$ being a ($C_1$-$C_6$) alkyl group optionally substituted by an amino group at the end of the alkyl chain.

In a very particular aspect, the compound of formula (I) is selected in the group consisting of:
2-[2-[4-[2-methyl-3-(10H-phenothiazin-10-yl)propyl]-1-piperazinyl]ethoxy]ethanol;
2-[4-[3-[2-(trifluoromethyl)-10H-phenothiazin-10-yl]propyl]-piperazin-1-yl]ethanol (compound 3);
2-[4-[3-(2-chloro-10H-phenothiazin-10-yl) propyl]piperazin-1-yl]ethanol (compound 1);
2-(4-(3-(2-Chloro-10H-phenothiazin-10-yl)propyl)piperazin-1-yl)ethyl heptanoate;
2-chloro-10-[3-(4-methyl-1-piperazinyl)propyl]-10H-phenothiazine (compound 2);
2-[4-[3-(2-chloro-10H-phenothiazin-10-yl)propyl]piperazin-1-yl]ethyl acetate;
10-[3-(4-methylpiperazin-1-yl)propyl]-2-(trifluoromethyl)-10H-phenothiazine (compound 4);
2-(ethylthio)-10-[3-(4-methylpiperazin-1-yl)propyl]-10H-phenothiazine (compound 8);
1-[10-[3-[4-(2-hydroxyethyl)piperazin-1-yl]propyl]-10H-phenothiazin-2-yl]ethanone (compound 5);
N,N-dimethyl-10-[3-(4-methylpiperazin-1-yl)propyl]-10H-phenothiazine-2-sulfonamide (compound 6);
1-[10-[3-(4-methylpiperazin-1-yl)propyl]-10H-phenothiazin-2-yl]butan-1-one; and
10-[3-(4-methylpiperazin-1-yl)propyl]-10H-phenothiazine (compound 7).

In a particular embodiment, the compounds of the invention are used for treating spasticity following an ischemia or a traumatic injury, or a compression syndrome.

In yet another particular embodiment, the compounds of the invention are used for treating neuropathic pain following an ischemia or a traumatic injury, or a compression syndrome.

DETAILED DESCRIPTION OF THE INVENTION

The inventors identified a new use of compounds of general formula (I), which correspond to piperazine phenothiazine derivatives:

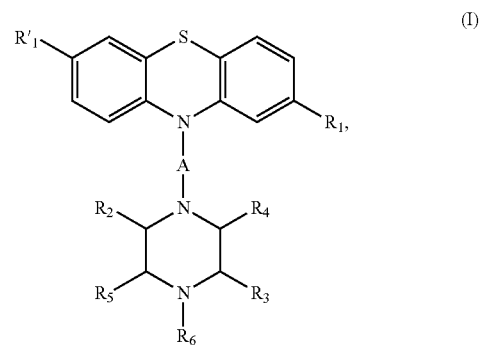

(I)

having a therapeutic interest for treating spasticity.

Specifically, the inventors surprisingly discovered that phenothiazine derivatives substituted by a piperazine-derived substituent activate KCC2 by boosting KCC2 potassium/chloride transport, KCC2 expression and/or by modulating the subcellular localization of such transporter. The inventors also demonstrated that the compounds of the invention are able to reduce the intracellular concentration of chloride ions, spasticity and the chronic neuropathic pain, as a result of an up-regulation of KCC2 expression and function.

In particular, a better KCC2 activation profile is surprisingly observed with the compounds of the formula (I) of the present invention.

Accordingly, the present invention relates to a compound of formula (I) for use for treating spasticity or neuropathic pain:

(I)

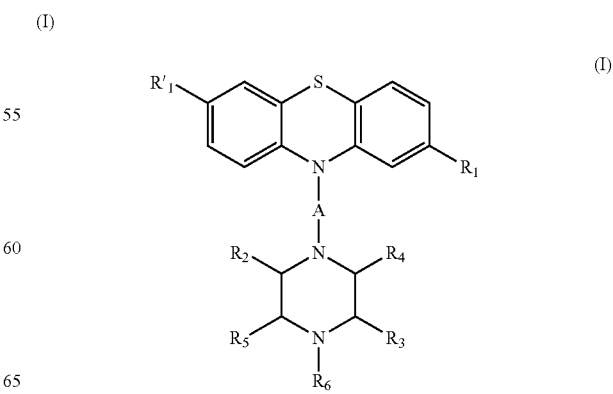

(I)

A represents a linear or branched $(C_1-C_6)$ alkyl chain;

$R_1$ represents:
- a hydrogen atom,
- a halogen atom,
- an acyl group CO—$R_7$ or a sulfonyl group $5O2$-$R_7$, wherein $R_7$ represents a $(C_1-C_6)$ alkyl group,
- a sulfonamide group $SO_2$—$NR_8R_9$, wherein $R_8$ and $R_9$ independently represent a hydrogen atom, or a $(C_1-C_6)$ alkyl group, or
- a $(C_1-C_6)$ alkyl, $(C_1-C_6)$ alcoxy, $(C_1-C_6)$ alkylmercapto, thio-$(C_1-C_6)$ alkyl, or $(C_1-C_6)$ alkylsulfonyl group, said groups being optionally substituted by at least one halogen atom;

$R_1'$ represents a hydrogen atom or an hydroxyl group, preferably a hydrogen atom;

$R_2$, $R_3$, $R_4$ and $R_5$ are identical or different and each represents a hydrogen atom or a $(C_1-C_6)$ alkyl group; and $R_6$ represents:
- a hydrogen atom,
- a $(C_1-C_6)$ alkyl group, optionally substituted by at least one hydroxyl group at the end of the alkyl chain,
- a $(C_1-C_4)$ alkylacyloxy group,
- a $(C_1-C_4)$ alkyl-$OR_{10}$ group, wherein $R_{10}$ represents:
  - a $(C_1-C_4)$ alkyl group, optionally substituted by at least one hydroxyl group at the end of the chain, or
  - a $COR_{11}$ group, $R_{11}$ being a $(C_1-C_6)$ alkyl group optionally substituted by an amino group at the end of the alkyl chain;

or one of its pharmaceutically acceptable salts.

According to the present invention, the terms below have the following meanings:

The terms mentioned herein with prefixes such as for example $C_1-C_3$, $C_1-C_4$, $C_1-C_6$, can also be used with lower numbers of carbon atoms such as $C_1-C_2$, $C_1-C_3$, $C_1-C_6$ or $C_3-C_4$. If, for example, the term $C_1-C_3$ is used, it means that the corresponding hydrocarbon chain may comprise from 1 to 3 carbon atoms, especially 1, 2 or 3 carbon atoms. If, for example, the term $C_1-C_6$ is used, it means that the corresponding hydrocarbon chain may comprise from 1 to 6 carbon atoms, especially 1, 2, 3, 4, 5 or 6 carbon atoms. If, for example, the term $C_3-C_4$ is used, it means that the corresponding hydrocarbon chain may comprise 3 or 4 carbon atoms.

The term "alkyl" refers to a saturated, linear or branched hydrocarbon aliphatic group. The term "$(C_1-C_3)$alkyl" more specifically means methyl (also called "Me"), ethyl (also called "Et"), propyl, or isopropyl. The term "$(C_1-C_6)$alkyl" more specifically means methyl, ethyl, propyl, isopropyl, butyl, isobutyl, tert-butyl, pentyl or hexyl.

The term "alkylene" refers to an unsaturated linear or branched hydrocarbon aliphatic group. The term "propylene" refers an unsaturated linear or branched aliphatic group having 3 carbon atoms.

The term "alkoxy" or "alkyloxy" corresponds to the alkyl group defined hereinabove bonded to the molecule by an —O— (ether) bond. For instance, $(C_1-C_6)$alkoxy includes methoxy, ethoxy, propyloxy, isopropyloxy, butyloxy, isobutyloxy, tert-butyloxy, pentyloxy and hexyloxy.

The term "halogen" corresponds to a fluorine, chlorine, bromine, or iodine atom, preferably a chlorine or a fluorine atom, even more preferably a chlorine atom.

The expression "substituted by at least" or "substituted by" means that the radical is substituted by one or several groups of the list.

The term "amino" corresponds to a —$NH_2$ group.

The pharmaceutically acceptable salts include inorganic as well as organic acids salts. Representative examples of suitable inorganic acids include hydrochloric (or chlorhydric), hydrobromic, hydroiodic, phosphoric, and the like. Representative examples of suitable organic acids include formic, acetic, trichloroacetic, trifluoroacetic, propionic, benzoic, cinnamic, citric, fumaric, maleic, methanesulfonic and the like. The pharmaceutically acceptable salts of the compounds of the invention also include polysalts, for instance, polyhydrochlorate such as dihydrochlorate, trihydrochlorate, polymesylate such as di or tri-trimesylate, polymaleate such as di or tri-maleate.

Further examples of pharmaceutically acceptable inorganic or organic acid addition salts include the pharmaceutically acceptable salts listed in J. Pharm. Sci. 1977, 66, 2, and in Handbook of Pharmaceutical Salts: Properties, Selection, and Use edited by P. Heinrich Stahl and Camille G. Wermuth 2002.

In a preferred embodiment, the salt is selected from the group consisting of hydrochloride, maleate, and methanesulfonate (or mesylate). In a more preferred embodiment, the salt is selected from the group consisting of dihydrochloride, dimesylate, and dimaleate.

Phenothiazines are known as neuroleptic drugs for their effects as relieving schizophrenic agitation and maniacal behavior. Several phenothiazine derivates obtained a marketing authorization as antipsychotic, antiemetic, antiparkinson and antimigrainic. Particularly, the piperazine series are the most representative of phenothiazine antipsychotic compounds. Phenothiazine drugs have existed for at least forty years and targets, mechanism of action, compliance, side effects thereof have been investigated and developed.

Callizot and Collin (WO 2004/0962312) reported the use of piperazine phenothiazine derivatives having neuroproctector and/or neurotrophic effects on central nervous system (CNS) and/or peripheral nervous system, particularly for treating central and peripheral neurodegenerative diseases as Parkinson's disease, Alzheimer's disease or peripheral neuropathy diseases as amyotropic lateral sclerosis (ALS) diseases.

However, the use of piperazine phenothiazine derivatives for treating spasticity has never been disclosed or suggested in the prior art, notably by activation of KCC2 transporter. Moreover, the use of these compounds has never been described in the treatment of neuropathic pain via a mechanism involving the activation of KCC2.

Particularly, A represents a linear or branched $(C_3-C_4)$ alkyl chain, preferably a propyl or an isobutyl chain.

Preferably, $R_1$ represents:
- a hydrogen atom,
- a halogen atom,
- an acyl group CO—$R_7$ or a sulfonyl group $SO_2$—$R_7$, wherein $R_7$ represents a $(C_1-C_6)$ alkyl group,
- a sulfonamide group $SO_2$—$NR_8R_9$, wherein $R_8$ and $R_9$ independently represent a hydrogen atom, or a $(C_1-C_6)$ alkyl group, or
- a $(C_1-C_6)$ alkyl, $(C_1-C_6)$ alcoxy, $(C_1-C_6)$ alkanoyl, $(C_1-C_6)$ alkylmercapto, thio-$(C_1-C_6)$ alkyl or $(C_1-C_6)$ alkylsulfonyl group, said groups being optionally substituted by at least one halogen atom.

More preferably, $R_1$ represents:
- a hydrogen atom,
- a halogen atom, preferably a chlorine atom,
- an acyl group CO—$R_7$, wherein $R_7$ represents $(C_1-C_6)$ alkyl group, preferably a methyl or a n-propyl group, a sulfonamide group SO$_2$—NR$_8$R$_9$, wherein R$_8$ and R$_9$ independently represent a hydrogen atom, or a (C$_1$-C$_6$) alkyl group, preferably R$_8$ and R$_9$ represent methyl groups, a (C$_1$-C$_6$) alkyl group optionally substituted by at least one fluorine atom, preferably a trifluoromethyl group, or a thio-(C$_1$-C$_6$) alkyl group, preferably a thio-ethyl (—SCH$_2$CH$_3$) group.

Even more preferably, R$_1$ represents:
a hydrogen atom,
a chlorine atom,
an acyl group CO—R$_7$, wherein R$_7$ represents a methyl or a n-propyl group,
a sulfonamide group SO$_2$—NR$_8$R$_9$, wherein R$_8$ and R$_9$ represent methyl groups, or
a trifluoromethyl, or a thio-ethyl (—SCH$_2$CH$_3$) group.

Advantageously, R$_1$ is a chlorine atom.

In a further embodiment, R$_1$', R$_2$, R$_3$, R$_4$ and R$_5$ represent hydrogen atoms. In this particular embodiment, the piperazinyl cycle is substituted by a R$_6$ substituent only.

In another particular embodiment, R$_6$ represents:
a hydrogen atom,
a (C$_1$-C$_6$) alkyl group optionally substituted by at least one hydroxyl group at the end of the alkyl chain,
a (C$_1$-C$_4$) alkylacyloxy group,
a (C$_1$-C$_4$) alkyl-OR$_{10}$ group, wherein R$_{10}$ represents:
  a (C$_1$-C$_4$) alkyl group optionally substituted by at least one hydroxy group at the end of the chain, or
  a COR$_{11}$ group, R$_{11}$ being a (C$_1$-C$_6$) alkyl group optionally substituted by an amino group at the end of the alkyl chain.

Preferably, R$_6$ represents
a (C$_1$-C$_6$) alkyl group, preferably a methyl or ethyl group, optionally substituted by at least one hydroxyl group at the end of the alkyl chain,
an ethyl group substituted by an —OR$_{10}$ unit wherein R$_{10}$ preferably represents:
  an ethyl optionally substituted by at least one hydroxyl group at the end of the alkyl chain, or
  a COR$_{11}$ group, R$_{11}$ being a (C$_1$-C$_6$) alkyl group optionally substituted by an amino group at the end of the alkyl chain.

Even more preferably, R$_6$ represents an ethyl group substituted by a hydroxyl at the end of the alkyl chain or a methyl group.

In an advantageous embodiment, A represents a linear propyl chain, R$_1$ is a chlorine atom, R$_1$', R$_2$, R$_3$, R$_4$ and R$_5$ are hydrogen atoms and R$_6$ represents an ethyl group substituted by a hydroxyl group at the end of the alkyl chain or a methyl group.

In a very particular aspect, the compounds for use are selected in the group consisting of:
2-[2-[4-[2-methyl-3-(10H-phenothiazin-10-yl)propyl]-1-piperazinyl]ethoxy]ethanol;
2-[4-[3-[2-(trifluoromethyl)-10H-phenothiazin-10-yl]propyl]-piperazin-1-yl]ethanol;
2-[4-[3-(2-chloro-10H-phenothiazin-10-yl) propyl]piperazin-1-yl]ethanol;
2-(4-(3-(2-Chloro-10H-phenothiazin-10-yl)propyl)piperazin-1-yl)ethyl heptanoate;
2-chloro-10-[3-(4-methyl-1-piperazinyl)propyl]-10H-phenothiazine;
2-[4-[3-(2-chloro-10H-phenothiazin-10-yl)propyl]piperazin-1-yl]ethyl acetate;
10-[3-(4-methylpiperazin-1-yl)propyl]-2-(trifluoromethyl)-10H-phenothiazine;
2-(ethylthio)-10-[3-(4-methylpiperazin-1-yl)propyl]-10H-phenothiazine;
1-[10-[3-[4-(2-hydroxyethyl)piperazin-1-yl]propyl]-10H-phenothiazin-2-yl]ethanone;
N,N-dimethyl-10-[3-(4-methylpiperazin-1-yl)propyl]-10H-phenothiazine-2-sulfonamide;
1-[10-[3-(4-methylpiperazin-1-yl)propyl]-10H-phenothiazin-2-yl]butan-1-one; and
10-[3-(4-methylpiperazin-1-yl)propyl]-10H-phenothiazine.

Preferably, the compounds for use are illustrated in FIG. 1A and are selected in the group consisting of:
2-[4-[3-[2-(trifluoromethyl)-10H-phenothiazin-10-yl]propyl]-piperazin-1-yl]ethanol;
2-[4-[3-(2-chloro-10H-phenothiazin-10-yl) propyl]piperazin-1-yl]ethanol;
2-chloro-10-[3-(4-methyl-1-piperazinyl)propyl]-10H-phenothiazine;
10-[3-(4-methylpiperazin-1-yl)propyl]-2-(trifluoromethyl)-10H-phenothiazine;
2-(ethylthio)-10-[3-(4-methylpiperazin-1-yl)propyl]-10H-phenothiazine;
1-[10-[3-[4-(2-hydroxyethyl)piperazin-1-yl]propyl]-10H-phenothiazin-2-yl]ethanone;
N,N-dimethyl-10-[3-(4-methylpiperazin-1-yl)propyl]-10H-phenothiazine-2-sulfonamide; and
10-[3-(4-methylpiperazin-1-yl)propyl]-10H-phenothiazine.

Even more preferably, the compound for use is selected in the group consisting of:
2-[4-[3-(2-chloro-10H-phenothiazin-10-yl) propyl]piperazin-1-yl]ethanol; and
2-chloro-10-[3-(4-methyl-1-piperazinyl)propyl]-10H-phenothiazine.

Pharmaceutical Use

The present invention also concerns a pharmaceutical composition comprising at least one compound of formula as defined above including anyone of the disclosed embodiments, and a pharmaceutically acceptable carrier for use for treating spasticity, particularly following an ischemia or traumatic injury, or a compression syndrome.

The present invention also concerns a pharmaceutical composition comprising at least one compound of formula as defined above including anyone of the disclosed embodiments, and a pharmaceutically acceptable carrier for use for treating neuropathic pain.

In a particular embodiment, the pharmaceutical composition comprises an additional compound for treating pain or spasticity.

Said additional compound may for example be chosen in the group comprising, but not limited to baclofen, tizanidine, dantrolene sodium, cyclobenzaprine, onabotulinumtoxinA, abobotulinumtoxinA, incobotulinumtoxinA, morphine, gabapentin, pregabaline (Lyrica), clonazepam, diazepam (Valium), ketamin, trihexyphenidyle chlorhydrate, and/or pridinol. Said additional compound may more particularly activate the KCC2 transporter. In that context, the additional compound is preferably another compound of formula (I) The pharmaceutical composition of the invention is more specifically for a simultaneous, separate or sequential administration of the said compounds, i.e, a compound of formula (I) and an additional compound.

The pharmaceutical composition is then administered orally or non-orally, for instance via the parenteral, intravenous, cutaneous, nasal, or via aerosol delivery to a patient. If the compounds are formulated independently, the corresponding formulations can be mixed together extemporaneously, using for instance a diluent, and are then administered or can be administered independently of each other, either successively or sequentially, and possibly by different routes of administration, such as for instance one by oral route and the other by injection.

The present invention further concerns the use of a pharmaceutical composition as defined above or a compound of formula (I) as defined above including anyone of the disclosed embodiments, for the manufacture of a medicament for the treatment of spasticity, particularly following an ischemia or traumatic injury, or a compression syndrome.

The present invention further concerns the use of a pharmaceutical composition as defined above or a compound of formula (I) as defined above including anyone of the disclosed embodiments, for the manufacture of a medicament for the treatment of neuropathic pain.

The present invention also relates to a method for treating spasticity, particularly following an ischemia or traumatic injury, or a compression syndrome, comprising administering an effective amount of a compound of formula as defined above including anyone of the disclosed embodiments or a pharmaceutical composition as defined above in a patient in need thereof.

In a particular embodiment, said method further comprises administering an effective amount of another compound for treating spasticity and/or pain. The said another compound can be defined as above.

More particularly, the invention relates to a method to activate KCC2 transport or KCC2 expression, and/or to modulate the subcellular localization of KCC2 transporter, and/or to reduce the intracellular concentration of chloride ions, comprising administering an effective amount of at least a compound of formula (I) as defined above including anyone of the disclosed embodiments or a pharmaceutical composition as defined above in a patient in need thereof.

As used herein, the term "patient" refers to any subject (preferably human) afflicted with or susceptible to be afflicted with spasticity or possibly neuropathic pain.

The term "spasticity", as used herein corresponds to any uncontrolled and involuntary contraction of one or more skeletal muscles of many common disease conditions.

As used herein, the term "neuropathic pain" is defined as pain arising as a direct consequence of a lesion or disease affecting the central or peripheral nervous system. Neuropathic pain may result from an ischemia, a traumatic injury or a compression syndrome.

In a particular embodiment, spasticity results from traumatic or ischemic neuropathies, or a compression syndrome.

Examples of "ischemic injuries", as used in the context of the present invention include any cardiovascular accident and/or spinal cord ischemia.

Examples of "traumatic injuries", as used in the context of the present invention include cranial (or brain) or spinal cord injury, peripheral nerve injury.

Examples of "compression syndromes", as used in the context of the present invention include nerve compression, such as disc herniation-induced nerve compression, typically disc herniation-induced spinal nerve compression.

In a particular embodiment, the compounds of the invention are used for treating spasticity following an ischemic or traumatic primary injury, preferably brain injury, spinal injury, and/or peripheral nerves injury.

In addition to the treatment of spasticity following an ischemic or traumatic primary injury, the invention may also be used for treating neuropathic pain following nerve compression, preferably disc herniation-induced nerve compression.

By "treatment" is meant the curative treatment and the prophylactic treatment of spasticity or pain. A curative treatment is defined as a treatment that eases, improves and/or eliminates, reduces and/or stabilizes spasticity, suffering or pain. A prophylactic treatment comprises a treatment that prevents pain or spasticity after a traumatic or ischemic injury, as well as a treatment that reduces and/or delays spasticity or pain or the risk of the occurrence of pain or spasticity.

By "effective amount" it is meant the quantity of the compound as defined above or the pharmaceutical composition comprising the same which prevents, removes or reduces the deleterious effects of the treated disease in humans. It is understood that the administered dose may be adapted by those skilled in the art according to the patient, the pathology, the mode of administration, etc. For instance, the compounds of the invention may be used at a dose of 0.0001 to 5000 mg/day for a human patient. In a particular embodiment, the pharmaceutical composition according to the invention comprises 0.01 to 500 mg of the compound of the invention, preferably between 0.1 and 500 mg/day, more preferably between 2 and 200 mg/kg/day.

In a particular aspect, the compounds of the invention can be administered by oral route or intramuscular injection at a daily dose of between 0.1 and 500 mg, preferably 2 and 200 mg. They can be administered 4, 5, 6 or 7 days a week during 1, 2, 3, 4, 5, 6 or 7 weeks. Optionally, several treatment cycles can be performed, optionally with a break period between two treatment cycles, for instance of 1, 2, 3, 4 or 5 weeks.

The administration route can be topical, transdermal, oral, rectal, sublingual, intranasal, intrathecal, intratumoral or parenteral (including subcutaneous, intramuscular, intravenous and/or intradermal). Preferably, the administration route is parental or oral. The pharmaceutical composition is adapted for one or several of the above-mentioned routes.

The pharmaceutical composition is preferably administered by injection or by intravenous infusion or suitable sterile solutions, or in the form of liquid or solid doses via the alimentary canal.

The pharmaceutical composition can be formulated as solutions in pharmaceutically compatible solvents or as emulsions, suspensions or dispersions in suitable pharmaceutical solvents or vehicles, or as pills, tablets or capsules that contain solid vehicles in a way known in the art.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations suitable for parenteral administration conveniently comprise a sterile oily or aqueous preparation of the active ingredient which is preferably isotonic with the blood of the recipient. Every such formulation can also contain other pharmaceutically compatible and non-toxic auxiliary agents, such as, e.g. stabilizers, antioxidants, binders, dyes, emulsifiers or flavouring substances.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof. The pharmaceutical compositions are advantageously applied by injection or intravenous infusion of suitable sterile solutions or as oral dosage by the digestive tract. Methods for the safe and effective administration of most of these chemotherapeutic agents are known to those skilled in the art. In addition, their administration is described in the standard literature.

LEGEND TO THE FIGURES

FIG. 1A: Chemical structure of piperazine phenothiazines-derived compounds 1 to 8.

FIG. 1B: Cytotoxicity of piperazine phenothiazines-derived compounds 1 to 8. Cytotoxicity were evaluated with fluorescent viability assay on HEK cells lines incubated 1 h with several concentrations of drugs. TC50: Toxic Concentration for 50% of the population.

FIG. 1C: Comparison of the effect of 8 compounds at 30 µM on KCC2 activity. Data are normalized to untreated (i.e. no drug, only DMSO). The effect of each drug was normalized to the maximal effect obtained with the compound 1, perphenazine (100%).

FIG. 1D: Dose response curve obtained for compound 1 (perphenazine) (a) and compound 2 (Prochlorperazine) (b) on HEK Wt and HEK KCC2.±s.d. based on three independent experiments (n=3).

Figure 2A:
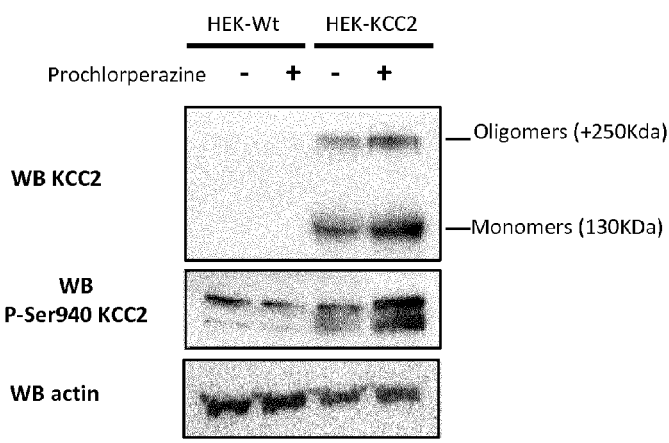

FIG. 2A: Detection by western-blot of KCC2 in total cell lysate extract from HEK Wt and HEK KCC2 treated with prochlorperazine (compound 2) or DMSO (−).

Figure 2B:
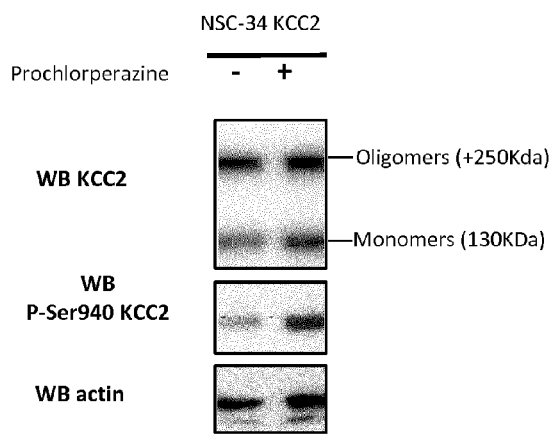

FIG. 2B: Detection by western-blot of KCC2 in total cell lysate extract from NSC-34 KCC2 treated with prochlorperazine (compound 2) or DMSO (−).

FIG. 3 A: Hyperpolarizing shift of EIPSP induced by prochlorperazine (compound 2) in lumbar MNs in neonatal P4-6 rats. $E_{IPSP}$ (a), $V_{rest}$ (b) and driving force ($E_{IPSP}-V_{rest}$; (c)) measured from rats before (CTL) and after 20-25' Prochlorperazine (2) (10 µM, n=6; *p<0.05 Wilcoxon test).

FIG. 3 B: Prochlorperazine (compound 2) induces a dose-dependent strengthening of reciprocal inhibition in the in vitro spinal cord preparation isolated from P5-7 animals with a spinal cord transection at birth. Error bars represent s.e.m; n=6 in each group.

Figure 4:
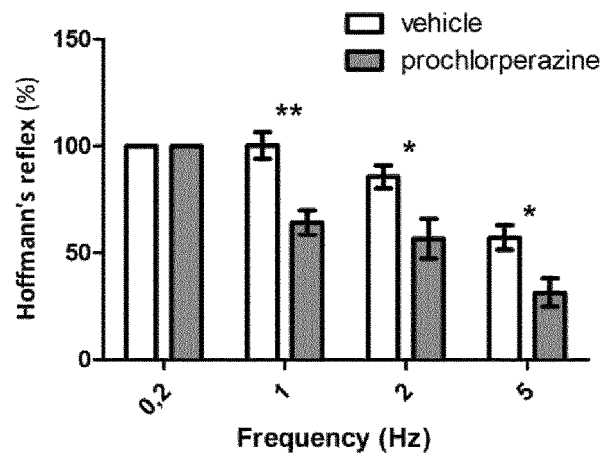

FIG. 4: Effect of prochlorperazine (compound 2) on spasticity. Rate-dependent depression of the Hoffman (H) reflex evoked in adult rats 4 weeks after SCI, 80 minutes after injection of 10 µg/kg of prochlorperazine (2) (i.v.) (n=6) or vehicle (n=5). Error bars represent s.e.m (p<0.05 Mann Whitney test at each frequency). Prochlorperazine (2) reduces spasticity after spinal cord injury.

Figure 5:
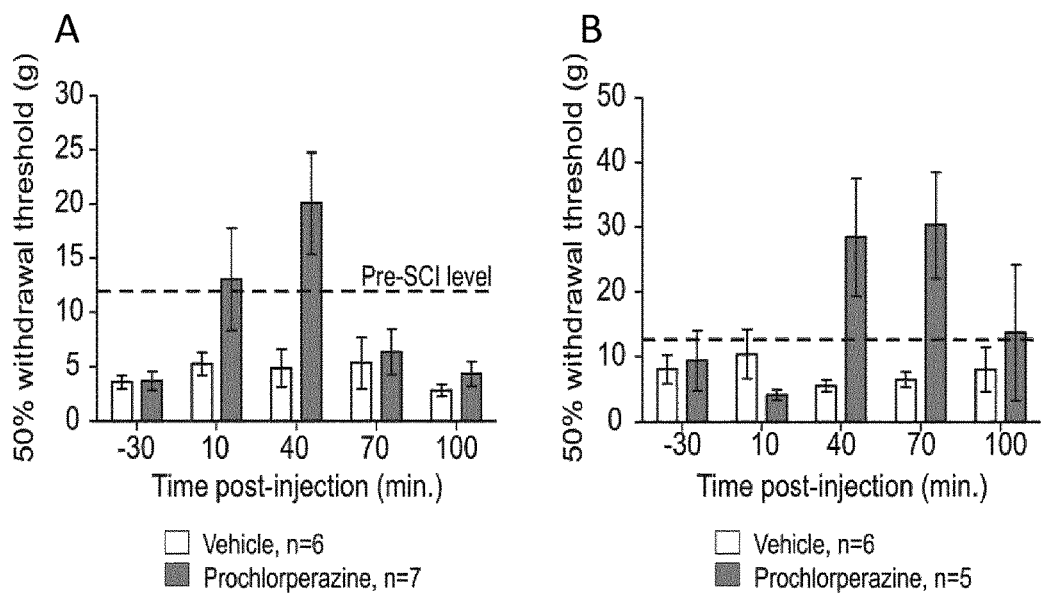

FIG. 5: Effect on the paw withdrawal thresholds in response to mechanical stimulation with prochlorperazine (compound 2). Prochlorperazine (2) (or placebo) was injected intraperitoneally (2 mg/kg) (FIG. 5 A) or intravenously (50 ng/kg) (FIG. 5 B) to Wistar rats, 21 days after the injury. The pain thresholds were determined before and 10, 40, 70 and 100 minutes after drug injection. Error bars represent s.e.m. Prochlorperazine (2) reduces mechanical hyperalgesia after spinal cord injury.

Further aspects and advantages of the invention will be disclosed in the following experimental section.

EXAMPLES

Example 1: Specific Activation of the Potassium Chloride Co-Transporter KCC2 with Compound 1-8

1. Materials and Methods 1.1. Compounds

Chemical structure of compounds 1-8 is illustrated in FIG. 1A. Compounds 1-4, 6 and 8 were purchased from Prestwick Chemical. Compound 5 was purchased from Sigma Aldrich (St Louis, Mo., USA) and compound 7 was purchased from Santa Cruz Biotechnology (Dallas, Tex., USA). All of these compounds are provided in DMSO solution (under argon) and frozen for storage and are supplied at a precise 20 mM concentration.

1.2. Cellular Model and Cell Culture

Wild-type or KCC2-expressing Human Embryonic Kidney (HEK) 293 cells (provided by Prof. Eric Delpire Department of Anesthesiology, Vanderbilt University Medical Center, Nashville, Tenn.) were grown up to 80-90% confluence in DMEM/Ham's F-12 (1:1) (Life technologies, Carlsbad, Calif., USA) supplemented with 10% FBS (Life technologies), 50 units/mL penicillin, and 50 pg/mL streptomycin (Life technologies). KCC2-expressing clones were under puromycin selection (20 µg/ml, Life technologies).

1.3. Fluorescence Based Thallium ($Tl^+$) Influx Assay

The FluxOR™ potassium ion channel assay (Life Technologies Carlsbad, Calif., USA) was performed as outlined in the product information sheet and an earlier published study (Delpire et al., 2009, Proc. Natl. Acad. Sci. USA, 106, 5383-88) to assess KCC2 activity, and adapted to semi-automated high throughput screening. The experiment was performed in the presence of ouabain 200 µM and bumetanide 10 µM in all buffers to block the $Na^+/K^+$ pump and NKCC1 cotransporters, respectively. Briefly, cells in suspension were incubated in the loading buffer containing the dye at room temperature for 90 min (1/2000 dilution of FluxOR reagent) at the density of 100.000 cells/75 µl, then centrifugated and resuspended in Assay buffer at the same cell density. A number of 100.000 cells (75 µl) were manually handled in each well to the 96-wells black-walled, µclear-bottom plates (Greiner Bio-One, Monroe, N.C., USA) and 5 µl of chemical compounds 1-8 at different concentrations in PBS 1% DMSO (5, 30 and 50 µM) were added to the plates using the Biomek® NX Laboratory automation workstation (Beckman Coulter, Villepinte, France). After 15 minutes incubation, baseline fluorescent signal was measured with the Polarstar omega microplate reader (490 nm excitation and 520 nm emission, BMG Labtech). Then 20 µL per well of 5× thallium stimulus buffer (final concentrations: $Tl^+$: 2 mM, $K^+$: 10 mM) was injected and fluorescent signal was read 30 minutes later.

For each plate, 2 columns were dedicated to controls (cell density range from 0.25 to $1.10^5$ cells; loading buffer as blank; untreated or treated with NEM (33 µM, for 15 min) wild-type and KCC2-expressing HEK293 cells).

1.4. Cell Viability Assay

After stimulus buffer induced signal acquisition, PrestoBlue® Cell Viability Reagent (Life technologies), a cell permeable resazurin-based solution was used according to manufacturer procedure as a cell viability indicator (Excitation/Emission (nm): 535-560/590-615). A fluorescence curve produced using the range of cell numbers was then used to define an equation to calculate the number of cells alive in each well and thereby to evaluate the cytotoxicity of compounds 1-8.

1.5. Data Analysis

Baseline fluorescent value was subtracted from the fluorescent value measured 30 min after stimulus buffer injection for each well, and this difference was normalized to the number of cells. Compounds displayed selective activity on KCC2-expressing cells with treated cells/untreated cells signal ratio >1.10 and slight effect on wild-type cells (treated cells/untreated cells signal ratio=1±0.2). Values converted to percentages such that the maximum of ratio is 100%.

2. Results

The results of FluxOR fluorescent assay for each compound are illustrated in FIG. 1C. (−) represent control assay (i.e. no drug, only DMSO) and cytotoxic concentrations have been excluded and only data for up to 70% viability of cells in FIG. 1B have been considered. The inventors have demonstrated that all the compounds (1)-(8) enhance KCC2 activity with different efficiencies: the strongest effects were obtained with perphenazine (1) at 30 μM (100%) and perazine (7) (55%). No results was obtained with thiethylperazine dimaleate (8) at 30 μM as it was cytotoxic at this concentration.

Effects of perphenazine (1) and prochlorperazine (2) on KCC2-expressing HEK cells compared to WT HEK cells across a dose range, chosen on the basis of lack of cytotoxicity, have also been evaluated (FIG. 1D).

The inventors have demonstrated that compounds of the invention, particularly compounds (1) perphenazine and (2) prochlorperazine activate specifically KCC2 in a dose dependant manner.

Example 2: Promoting of KCC2 Expression with Prochlorperazine (2)

1. Materials and Methods
1.1. Cellular Model and Cell Culture

Wild-type or KCC2-expressing Human Embryonic Kidney (HEK) 293 cells (provided by Prof. Eric Delpire Department of Anesthesiology, Vanderbilt University Medical Center, Nashville, Tenn.) were grown up to 80-90% confluence in DMEM/Ham's F-12 (1:1) (Life technologies, Carlsbad, Calif., USA) supplemented with 10% FBS (Life technologies), 50 units/mL penicillin, and 50 pg/mL streptomycin (Life technologies). KCC2-expressing clones were under puromycin selection (20 μg/ml, Life technologies).

The NSC-34 motor neuron cell line (CELutions Biosystem Inc, Ontario) which does not express KCC2 endogenously, were infected with lentivirus derived from the human immunodeficiency virus-1 (HIV-1) encoding KCC2 and cultures several week after clonal isolation to establish the NSC-34 KCC2 stable cell line. NSC-34 wild type and KCC2 were cultured in DMEM (Life technologies, Carlsbad, Calif., USA) supplemented with 10% FBS (Life technologies), 50 units/mL penicillin, and 50 pg/mL streptomycin (Life technologies).

1.2 Western Blot

Wild-type and KCC2-expressing HEK293 cells or NSC-34 were harvested and homogenised in lysis buffer (PBS containing 1% Igepal CA-630, 0.1% SDS, 10 mM sodium pyrophosphate, 10 mM NaF, 10 mM NaVO4, 10 mM iodoacetamide and cocktail protease inhibitors and centrifugated at 18000 g for 30 minutes at 4° C. Protein concentration in supernatants was determined using DC protein assay (Bio-rad). Same amounts of total proteins were separated in 6% or 7% SDS PAGE and transferred onto PVDF membrane. Once blocked in Tris Buffer Saline 0.05% Tween 5% non-fat dry milk, membranes were probes over night at 4° C. with KCC2 antibody (1/1000 dilution, Merck-Millipore, Billerica, Mass., USA), or anti-phospho-serine940 KCC2 (1/1000 dilution, PhosphoSolutions) or anti-Actin antibody (1/500 dilution, Sigma Aldrich). Anti-rabbit secondary antibody HRP conjugated was used for detection in chemiluminescent system (Thermo Scientific, Waltham, Mass., USA). Signal intensity was measured with the image analysis software Image lab (Bio-Rad, Hercules, Calif., USA).

2. Results

Prochlorperazine (2) effect (10 μM) on the total expression of KCC2 in HEK KCC2 and NSC-34 KCC2 cell lines has been tested by means of western blot analysis (FIGS. 2A and 2B, respectively).

In the whole cell lysate, the inventors have shown that both the total KCC2 protein level (monomers+oligomers) and phosphorylated KCC2 on serine 940 increased after 30 min of cell treatment with prochlorperazine (2). According to these results, the inventors have demonstrated that compound (2) up-regulates the expression of the KCC2 protein in the HEK cells used for the screening but also in NSC34 cell line which present more neuronal characteristics.

Example 3: Electrophysiological Recordings and In Vivo Tests with Prochlorperazine

1. Materials and Methods
1.1. Animals

Neonatal and adult (150-250 g) female Wistar rats (Charles River, Burlington Mass. USA) were used. Animals were housed in a temperature-controlled animal care facility with a 12 h light-dark cycle. We made all efforts to minimize animal suffering and the number of animals used. Neonates were anesthetized by hypothermia. We performed experiments in accordance with French regulations (Ministry of Food, Agriculture and Fisheries, Division of Health and Protection of Animals). The local Direction of Veterinary Services and Ethical Committee (Marseille, Provence) delivered the appropriate licenses and approved the protocols, respectively.

1.2. Intracellular Recordings

Spinal cords isolated from neonatal rats on post natal day 4 or 5 were dissected together with spinal roots. Briefly, after decapitation and evisceration, the spinal cord was exposed by dorsal laminectomy and acute removal of the dura in a cold artificial cerebrospinal fluid (ACSF; containing (in mM): 130 NaCl, 4 KCl, 3.75 $CaCl_2$, 1.3 $MgSO_4$, 0.58 $NaH_2PO_4$, 25 $NaHCO_3$ and 10 glucose (all compounds were from Sigma); oxygenated with 95% $O_2$/5% $CO_2$, pH=7.4). The cord, from sacral segments up to T8, was then removed from the vertebral column together with peripheral roots. The preparation was then transferred to the recording chamber where it was pinned down, ventral side up, in sylgard (Dow-Corning; USA)-covered recording chamber, and continuously perfused with the ACSF solution. After removing the pia, we recorded lumbar motoneurons (MNs) intracellularly using glass microelectrodes filled with 2 M K-acetate (70 to 100-MΩ resistance). We recorded intracellular potentials in the discontinuous current-clamp (DCC) mode (Axoclamp 2B amplifier; Digidata 1200 interface; pClamp9 software; Axon Instruments, Sunnyvale, Calif., USA). We used glass suction electrode to stimulate the ipsilateral ventral funiculus 2 to 3 segments rostral to the recorded one. Such stimulations induced $GABA_A$- and Gly-mediated Inhibitory Postsynaptic Potentials (IPSPs) in the presence of DL-2-amino-5-phosphonovaleric acid (DL-APV, 50 μM) and 6-cyano-7-nitroquinoxaline-2,3-dione (CNQX, 10 μM) (Bos et al., 2013; Boulenguez et al., 2010; Jean-Xavier et al., 2006). We recorded IPSPs at various holding potentials (500-ms-long current pulses) and collected at least 20 values for each MN. We measured and plotted amplitudes of IPSPs against holding potentials and obtained $E_{IPSP}$ from the regression line.

1.3. Extracellular Recordings and Evaluation of Reciprocal Inhibition

Neonatal Spinal Cord Injury and Preparations for In Vitro Electrophysiology

Rats were deeply anesthetized by hypothermia at birth. A dorsal midline skin incision was made over the thoracic vertebra and the overlying fascia and muscles were retracted to expose the dorsal surface of the vertebrae. After a partial laminectomy, the spinal cord was completely transected at the T8 thoracic level with scissors. The lesion cavity was then filled with sterile absorbable local hemostat Surgicoll (Medical Biomaterial Products; Neustadt-Glewe, Germany). The skin incision was closed with sutures (PDSII 6.0, Ethicon; Johnson and Johnson; Brussels, Belgium) and covered by Steri-Strips (3M Health Care; St. Paul, Minn.). The whole surgical procedure took less tan 10 min after anesthesia. Sham-operated rats were treated in the same way except 5 the spinal cord transection. Following surgery, the neonates recovered 45 min in a warm environment maintaining the temperature at 35±1° C. Wounds were then cleaned and rats were kept in a warm environment for 40 min before returning to the nest.

Spinal cords isolated from neonatal rats were prepared as described in section 1.2 until "recording".

In Vitro Extracellular Recordings and Evaluation of Reciprocal Inhibition

Extracellular electrophysiological signals of lumbar VRs and DRs responses were recorded by contact stainless steel electrodes insulated from the bath with vaseline. Data were acquired through an AC coupled amplifier (bandwidth: 70 to 3 kHz) and a Digidata 1440A interface using the Clampex 10.2 software (Molecular Devices; Sunnyvale, Calif., USA).

Single pulses were delivered to the DR to evoke responses in the homonymous VR. We stimulated at 2-3 times the threshold (T) intensity that evoked an incoming volley in the DR. The current pulses (0.3 ms duration) required to elicit the maximal response varied among preparations (from 0.6 to 1.2 V). Stimulations were delivered every 20 s to avoid fatigue and synaptic depression described in this preparation (Lev-Tov and Pinco, 1992). Test and conditioning stimulations were delivered to the L5 and L3 DRs, respectively. Delays between the two stimulations ranged from 0 to 40 ms. Each delay was tested at least two times in the following way: 5 controls (test only) followed by five paired (conditioning+test) stimulations. The order in which delays were tested was randomized from series to series to prevent possible order-dependent effects. Data analysis was performed offline and consisted in measuring the peak-to-antipeak amplitude of the L5 monosynaptic reflex (Clampfit 10.2 software). To consider only the monosynaptic component, we restricted measurements to the first 3 ms after the response onset (Kudo and Yamada, 1987).

1.4. Assessment of Spasticity Following Spinal Cord Injury Surgery:

Thoracic spinal section in rats was used as a model of SCI. Adult female Wistar Rats (225/250 g Charles River) were anaesthetized intraperitoneally with 50 mg/kg ketamine (Imalgen®, Merial, Duluth, Ga., USA) and 0.25 mg/kg Medetomidine (Domitor®, Janssen Pharmaceutica, Beerse, Belgium). The antibiotic Amoxycyline (Duphamox LA®, Pfizer, 150 mg/kg) was injected subcutaneously before the surgery. The skin was cut longitudinally over T8-T10 vertebra and a local anesthetic (2% Procaine hydrochloride, Pharmy H, Saint-Germain-en-Laye, France) was injected intramuscularly before cuting the paravertebral muscles. A laminectomy was performed at vertebral segment T9. The spinal cord was transected with microscissors at the level of the T8 spinal segment. Finally, paravertebral muscles and skin were sutured and rats were treated with buprenorphine for analgesia (1 injection before awakening from anaesthesia and 4 more injections over the next 48 h period). The rats weight, temperature and water intake were checked and their bladder was emptied manually twice a day until recovery of autonomy.

In Vivo Electrophysiological Recordings and Treatment with Prochlorperazine (2).

At day 29 post lesion, the H reflex in the rats under ketamine anesthesia (100 mg/kg, i.p.) were measured using a pair of stainless steel needle electrodes transcutaneously inserted into the vicinity of the tibial nerve stimulation. The recording electrode was placed into the flexor digitorum muscle beneath the ankle and the reference electrode s. c. into the foot.

The H reflex was measured three times at frequencies of 0.2 Hz 1 Hz, 2 Hz and 5 Hz to have their baseline values. Then, rats were treated with either prochlorperazine di-maleate (2) (10 µg/kg i.v. in 0.1% DMSO, 0.9% NaCl, n=6) or its vehicle (0.1% DMSO, 0.9% NaCl, n=5). The H reflex was measured each 20 minutes, five times at frequencies of 0.2 Hz 1 Hz, 2 Hz and 5 Hz 1.5. Behavioural Testing Following Spinal Cord Injury Surgery:

Thoracic spinal unilateral hemisection in rats was used as a model of SCI. Adult female Wistar Rats (Charles River) were anaesthetized intraperitoneally with 50 mg/kg ketamine (Imalgen®, Merial, Duluth, Ga., USA) and 0.25 mg/kg Medetomidine (Domitor®, Janssen Pharmaceutica, Beerse, Belgium). The antibiotic Amoxycyline (Duphamox LA®, Pfizer, 150 mg/kg) was injected subcutaneously before the surgery. The skin was cut longitudinally over T8-T10 vertebra and a local anesthetic (2% Procaine hydrochloride, Pharmy H, Saint-Germain-en-Laye, France) was injected intramuscularly before cuting the paravertebral muscles. A laminectomy was performed at vertebral segment T9. The spinal cord was hemisected on the left side with microscissors at the level of the T8 spinal segment. Finally, paravertebral muscles and skin were sutured and rats were treated with buprenorphine for analgesia (1 injection before awakening from anaesthesia and 2 more injections over the next 24 h period). Aspirin was diluted in their water bottles for 3 days (aspegic, 200 mg in 150 ml). The rats weight, temperature and water intake were checked and their bladder was emptied manually twice a day until recovery of autonomy.

Treatment with Prochlorperazine (2).

At day 21 post lesion, the rats were tested once with Von Frey hair and plantar test in order to have their baseline values. Five min later they were treated with either prochlorperazine di-maleate (2) (2 mg/kg ip in 0.9% NaCl, or 50 ng/kg iv in 0.9% NaCl, 0.1% DMSO) or its vehicle The experimenters were blind to the treatment that the animals received. Then the effects of the drug was measured alternatively on mechanical and thermal hyperalgesia every 15 min, that is at 10, 30, 40, and 100 min after injection, respectively.

Von Frey test:

The plantar surface of the left, then right hind paws were probed using von Frey monofilaments £Bioseb, Paris, France) which apply different calibrated forces when they bent. The test started by applying a Von Frey hair of 8 g for 3 sec, and the 50% withdrawal thresholds of each hindlimb in response to tactile stimulation were measured using the up and down method (Chaplan et al., 1994).

2. Results 2.1 Hyperpolarization of EIPSP with Prochlorperazine (2) (Test In Vitro)

Figure 3A:
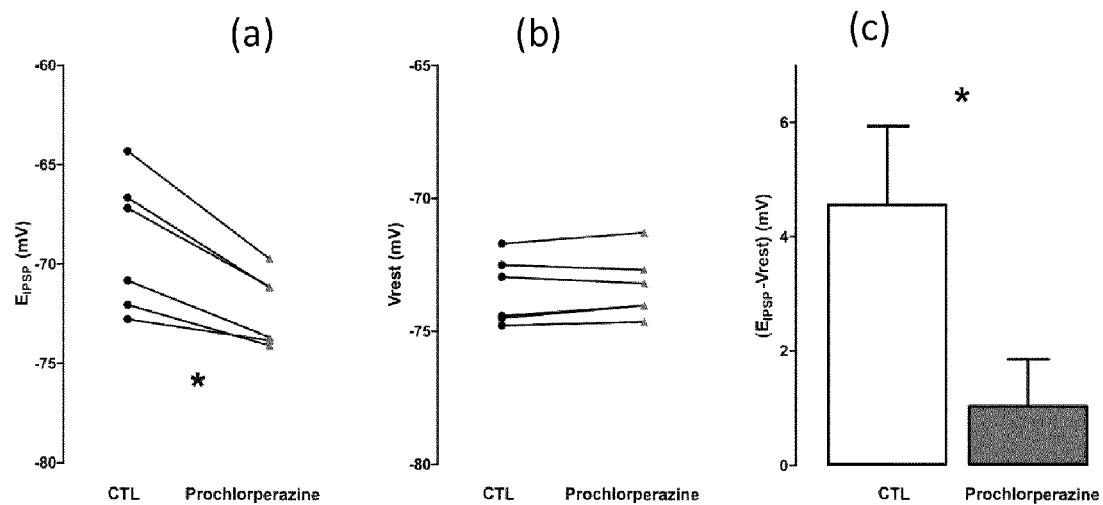
Figure 3B:
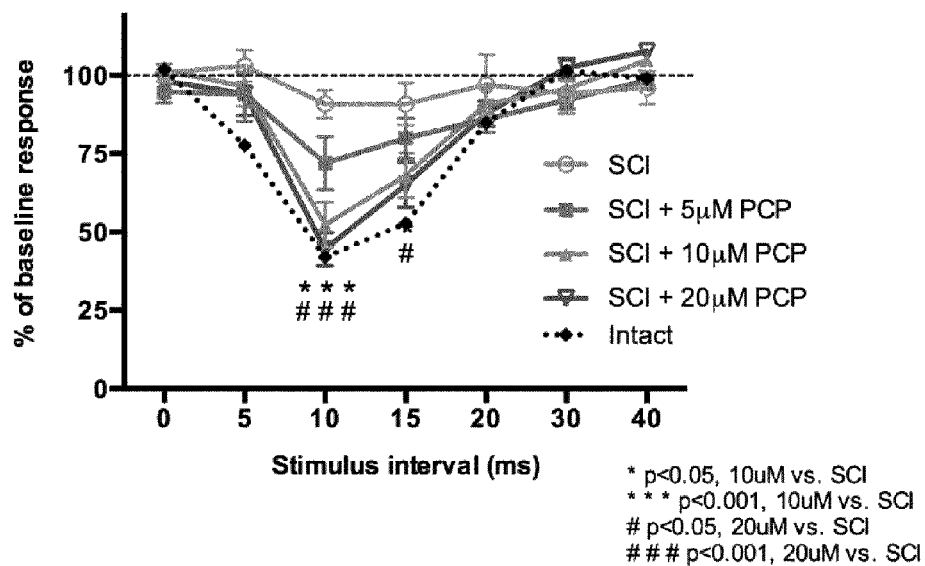

In the in vitro spinal cord preparation, isolated from neonatal rat, a way to investigate KCC2 function is provided by recording motoneurons (MNs) intracellularly and measuring the chloride equilibrium potential that is given by the reversal potential of inhibitory synaptic potentials ($E_{IPSP}$). The more hyperpolarized the value of $E_{IPSP}$, the lower the intracellular concentration of chloride ions and, as a result, the stronger the KCC2 function. The inventors have examined the effect of 10 µM Prochlorperazine (2) on $E_{IPSP}$ of lumbar MNs in P4-6 rats (FIG. 3). It hyperpolarized $E_{IPSP}$ within 5-10 min and measurements were done 20-25 min after the onset of Prochlorperazine (2) application. $E_{IPSP}$ was significantly more hyperpolarized when MNs were recorded in the presence of Prochlorperazine (2) compared to control conditions (mean of −3.3 mV; n=6; FIG. 3A; p<0.05, Wicoxon test). Prochlorperazine (2) has no significant impact on the resting membrane potential ($V_{rest}$; n=6; FIG. 3B; p>0.05, Wicoxon test). Therefore, the driving force increased significantly (mean of −3.5 mV; n=6; FIG. 3C; p<0.05, Wicoxon test). These results demonstrate that compound (2) is able to strengthen post-synaptic inhibition in the spinal cord by reducing the intracellular concentration of chloride ions as a result of an increased activity of KCC2.

2.2. Effect of Prochlorperazine (2) on Reciprocal Inhibition

The inventors have examined the effect of 5, 10 and 20 µM Prochlorperazine (2) on reciprocal inhibition of lumbar MNs (L3 and L5 segments) projecting to the limb flexor and extensor muscles, respectively (Nicolopoulos-Stournaras and Iles, 1983) in P5-7 rats (FIG. 3D). The spinal cord was transected on the day of birth, a protocol that reduces the strength of post-synaptic inhibition (compare SCI with intact). Measurements were done 20 min after the onset of Prochlorperazine (2) application. Prochlorperazine (2) significant increased the strength of reciprocal inhibition in a dose-dependent manner, so that an inhibition comparable to an intact spinal cord was observed with Prochlorperazine (2) at 200 µM (n=6; FIG. 3D; ANOVA).

2.3. Reduction of Spasticity by Prochlorperazine (2)

The Hoffmann reflex (H-reflex), a monosynaptic reflex mediated through the spinal cord, in neurologically intact and spastic individual record during electromyograms.

The H-reflex is commonly used to assess primary (type Ia) afferents-mediated motoneuronal excitability in individuals suffering from spasticity. Electromyograms typically show two responses, an initial M wave resulting from the direct activation of motor axons and a delayed H wave resulting from the monosynaptic activation of motoneurons by Ia afferents. The H wave magnitude is normally attenuated by repeated activations at frequencies higher than 0.2 Hz, with a more than 80% reduction at 5 Hz in rats. The H reflex is progressively increased in individuals with SCI, and this effect is a reliable correlate of the development of spasticity. Prochlorperazine (2) decreases the H reflex by ~30% at the different frequencies (Mann Whitney test p=0.0043, p=0.0303, p=0.0173, at 1, 2 and 5 Hz, respectively) 80 min after injection of 10 µg/kg, i.v. These data demonstrate that prochlorperazine (2) is a good candidate to treat spasticity after spinal cord injury (FIG. 4).

2.4. Reduction of Hyperlagesia by Prochlorperazine (2)

The Von Frey test is classically used to evaluate the effect of any treatment onto neuropathic pain, including that after spinal cord injury. This test measures the threshold of a mechanical stimulation that will induce paw withdrawal. This threshold is considerably reduced after spinal cord injury and reflects the hyperalgesia, a component of chronic pain. Results of Von Frey test showed that the acute administration of prochlorperazine (2) either intraperitoneally or intravenously temporarily reduces mechanical hyperalgesia in animals three weeks post-injury (FIG. 5). Effects were significant 40 minutes after the injection started.

CONCLUSION

The inventors have demonstrated that compounds of the invention are able on a cell model to boost potassium/chloride transport (as revealed by the FluxOR assay) and KCC2 cell expression.

The transfer to neurons in the spinal cord of neonatal mammals revealed that compounds of the invention are able to reduce the intracellular concentration of chloride ions (revealed by the hyperpolarizing shift of the chloride equilibrium potential), likely as a result of an up-regulation of KCC2 expression/function.

The translation to adult mammals in pathological conditions such as a spinal cord injury demonstrated that compounds of the invention are able to reduce spasticity and chronic neuropathic pain, likely by restoring endogenous inhibition, as an expected result of an upregulation of KCC2 expression/function.

These results confirm that KCC2 is a druggable target for the development of new therapeutic strategies to treat neuropathic pain and spasticity associated with trauma or compression syndromes (such as for instance persistent pain caused by disc herniation-induced nerve compression).

REFERENCES

Basso D M, Beattie M S, Bresnahan J C (1995) A sensitive and reliable locomotor rating scale for open field testing in rats. J Neurotrauma 12:1-21.

Bos R, Sadlaoud K, Boulenguez P, Buttigieg D, Liabeuf S, Brocard C, Haase G, Bras H, Vinay L (2013) Activation of 5-HT2A receptors upregulates the function of the neuronal K—Cl cotransporter KCC2. pp 348-353.

Boulenguez P, Liabeuf S, Bos R, Bras H, Jean-Xavier C, Brocard C, Stil A, Darbon P, Cattaert D, Delpire E, Marsala M, Vinay L (2010) Down-regulation of the potassium-chloride cotransporter KCC2 contributes to spasticity after spinal cord injury. Nat Med 16:302-307.

Chaplan S R, Bach F W, Pogrel J W, Chung J M, Yaksh T L (1994) Quantitative assessment of tactile allodynia in the rat paw. J Neurosci Methods 53:55-63.

Coull J A, Beggs S, Boudreau D, Boivin D, Tsuda M, Inoue K, Gravel C, Salter M W, de K Y (2005) BDNF from microglia causes the shift in neuronal anion gradient underlying neuropathic pain. Nature 438:1017-1021.

Coull J A, Boudreau D, Bachand K, Prescott S A, Nault F, Sik A, De Koninck P, De Koninck Y (2003) Trans-synaptic shift in anion gradient in spinal lamina I neurons as a mechanism of neuropathic pain. Nature 424:938-942.

Cramer S W, Baggott C, Cain J, Tilghman J, Allcock B, Miranpuri G, Rajpal S, Sun D, Resnick D (2008) The role of cation-dependent chloride transporters in neuropathic pain following spinal cord injury. Mol Pain 4:36.

Delpire E, Days E, Lewis L M, Mi D, Kim K, Lindsley C W, Weaver C D (2009) Small-molecule screen identifies inhibitors of the neuronal K—Cl cotransporter KCC2. Proc Natl Acad Sci USA 106:5383-5388.

Jean-Xavier C, Pflieger J-F, Liabeuf S, Vinay L (2006) Inhibitory post-synaptic potentials in lumbar motoneurons remain depolarizing after neonatal spinal cord transection in the rat. J Neurophysiol 96:2274-2281.

Kudo N, Yamada T (1987) Morphological and physiological studies of development of the monosynaptic reflex pathway in the rat lumbar spinal cord. The Journal of physiology 389:441-459.

Lev-Tov A, Pinco M (1992) In vitro studies of prolonged synaptic depression in the neonatal rat spinal cord. The Journal of physiology 447:149-169.

Lu Y, Zheng J, Xiong L, Zimmermann M, Yang J (2008) Spinal cord injury-induced attenuation of GABAergic inhibition in spinal dorsal horn circuits is associated with down-regulation of the chloride transporter KCC2 in rat. J Physiol 586:5701-5715.

Nicolopoulos-Stournaras S, Iles J F (1983) Motor neuron columns in the lumbar spinal cord of the rat. The Journal of comparative neurology 217:75-85.

Payne J A, Rivera C, Voipio J, Kaila K (2003) Cation-chloride co-transporters in neuronal communication, development and trauma. Trends Neurosci 26:199-206.

Vinay L, Jean-Xavier C (2008) Plasticity of spinal cord locomotor networks and contribution of cation-chloride cotransporters. Brain Res Rev 57:103-110.

Zhao B, Wong A Y, Murshid A, Bowie D, Presley J F, Bedford F K (2008) Identification of a novel di-leucine motif mediating K(+)/Cl(−) cotransporter KCC2 constitutive endocytosis. Cell Signal 20:1769-1779.

The invention claimed is:

1. A method for treating spasticity, comprising administering in a patient in need of such treatment an effective amount of a compound of formula (I):

(I)

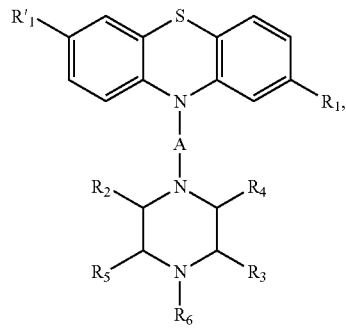

wherein:
A represents a linear propyl chain;
$R_1$ represents:
a hydrogen atom,
a halogen atom,
an acyl group CO—$R_7$, wherein $R_7$ represents a ($C_1$-$C_6$) alkyl group,
a sulfonamide group $SO_2$—$NR_8R_9$ wherein $R_8$ and $R_9$ independently represent a ($C_1$-$C_6$) alkyl group, or
a ($C_1$-$C_6$) alkyl optionally substituted by at least one halogen atom;
$R_1'$ represents a hydrogen atom;
$R_2$, $R_3$, $R_4$ and $R_5$ represent a hydrogen atom; and
$R_6$ represents:
a ($C_1$-$C_6$) alkyl group, optionally substituted by at least one hydroxyl group at the end of the alkyl chain,
or one of its pharmaceutically acceptable salts.

2. The method according to claim 1, wherein $R_1$ represents:
a hydrogen atom,
a chlorine atom,
an acyl group CO—$R_7$, wherein $R_7$ represents a methyl group,
a sulfonamide group $SO_2$—$NR_8R_9$ wherein $R_8$ and $R_9$ represent methyl groups, or
a ($C_1$-$C_6$) alkyl group optionally substituted by at least one fluorine atom.

3. The method according to claim 1, wherein $R_6$ represents:
a methyl or an ethyl group, optionally substituted by at least one hydroxyl group at the end of the alkyl chain.

4. The method according to claim 1, wherein said compound is selected in the group consisting of:
2-[4-[3-[2-(trifluoromethyl)-10H-phenothiazin-10-yl]propyl]-piperazin-1-yl]ethanol;
2-[4-[3-(2-chloro-10H-phenothiazin-10-yl) propyl]piperazin-1-yl]ethanol;
2-chloro-10-[3-(4-methyl-1-piperazinyl)propyl]-10H-phenothiazine;
10-[3-(4-methylpiperazin-1-yl)propyl]-2-(trifluoromethyl)-10H-phenothiazine;
1-[10-[3-[4-(2-hydroxyethyl)piperazin-1-yl]propyl]-10H-phenothiazin-2-yl]ethanone;
N,N-dimethyl-10-[3-(4-methylpiperazin-1-yl)propyl]-10H-phenothiazine-2-sulfonamide; and
10-[3-(4-methylpiperazin-1-yl)propyl]-10H-phenothiazine.

5. The method according to claim 1, wherein said compound is selected in the group consisting of:
2-[4-[3-(2-chloro-10H-phenothiazin-10-yl) propyl]piperazin-1-yl]ethanol; and
2-chloro-10-[3-(4-methyl-1-piperazinyl)propyl]-10H-phenothiazine.

6. The method according to claim 1, wherein the treatment of spasticity is the treatment of spasticity following an ischemia or a traumatic injury, or a compression syndrome.

7. The method according to claim 2, wherein the ($C_1$-$C_6$) alkyl group is optionally substituted by at least one trifluoromethyl group.

* * * * *